United States Patent [19]
Wenke et al.

[11] Patent Number: 5,961,991
[45] Date of Patent: *Oct. 5, 1999

[54] MELANOQUATERNARY COMPOUNDS AND THEIR USE AS HAIR DYES AND FOR SKIN TREATMENT

[75] Inventors: Gottfried Wenke, Woodbridge, Conn.; Giuseppe Prota, Naples, Italy

[73] Assignee: Bristol-Myers Squibb Company, New York, N.Y.

[ * ] Notice: This patent is subject to a terminal disclaimer.

[21] Appl. No.: 08/873,386

[22] Filed: Jun. 11, 1997

Related U.S. Application Data

[63] Continuation-in-part of application No. 08/568,056, Dec. 6, 1995, Pat. No. 5,702,712.
[51] Int. Cl.[6] ....................................................... A61K 7/48
[52] U.S. Cl. ........................... 424/401; 424/59; 424/70.1; 424/70.6; 8/405; 544/171; 546/238; 548/492
[58] Field of Search .............................. 548/492; 424/401, 424/59, 70.1, 70.6; 8/405; 544/171; 546/238

[56] References Cited

U.S. PATENT DOCUMENTS

| | | | |
|---|---|---|---|
| 5,006,331 | 4/1991 | Gaskin | 424/70 |
| 5,273,550 | 12/1993 | Prota et al. | 8/405 |
| 5,454,841 | 10/1995 | Wolfram et al. | 8/405 |
| 5,686,084 | 11/1997 | Wenke et al. | 424/401 |
| 5,702,712 | 12/1997 | Wenke et al. | 424/401 |

FOREIGN PATENT DOCUMENTS

| | | |
|---|---|---|
| WO 97/20541 | 6/1997 | WIPO . |
| WO 97/20542 | 6/1997 | WIPO . |

*Primary Examiner*—Jyothsna Venkat
*Attorney, Agent, or Firm*—Charles J. Zeller

[57] ABSTRACT

Water soluble, cationic products useful as hair colorants or for the treatment of skin which are esters or amides formed by reaction of melanin and a quaternary salt containing a reactive amino or hydroxyl group, as well as compositions containing them and methods of using such products to color hair or treat skin are described.

30 Claims, No Drawings

MELANOQUATERNARY COMPOUNDS AND THEIR USE AS HAIR DYES AND FOR SKIN TREATMENT

This application is a continuation- in- part of Ser. No. 08/568,056 filed Dec. 6, 1995 and now a U.S. Pat. No. 5,702,712.

BACKGROUND OF THE INVENTION

This invention relates to products, compositions and methods for coloring skin and hair utilizing water soluble quaternized melanin derivatives.

Naturally-occurring melanin is the pigment that gives hair its color. A general discussion of the properties and chemistry of melanins may be found in Prota, G., "Progress In The Chemistry of Melanins And Related Metabolites," *Med. Res. Reviews,* 8:525–56 (1988) and Moncrieff, R. W., *Manufacturing Chemist,* XXI, 8, 330–34 (August 1950). The gradual reduction of melanin formation with age causes hair to become gray.

Naturally-occurring melanin pigment itself is unacceptable for use in a hair dye composition because it is easily removed by rinsing or rubbing and leaves the hair feeling rough. In the past, one of the best methods for coloring gray hair involved the use of naturally-occurring melanin precursors (such as 5,6 dihydroxyindole (DHI)) that when combined with an oxidant or a metal salt, forms useful melanin pigments. See, for example, U.S. Pat. No. 3,194,734 (Seemuller et al.), U.S. Pat. No. 4,808,190 (Grollier et al.), and U.S. Pat. No. 4,888,027 (Grollier et al.).

However, the use of these melanin precursors has several disadvantages.

The primary disadvantage is that the pigments produced from melanin precursors provide undesirable achromatic colors (cold grays and blacks). Hair dyed with these colorants must undergo a second treatment step with an oxidant such as hydrogen peroxide to achieve natural chromatic colors (warm yellows, reds, and browns). See, for example, U.S. Pat. No. 3,194,734 (Seemuller et al.). In addition, melanin precursors are expensive and, because they are highly reactive, difficult to work with. The use of melanin precursors also can result in undesirable scalp and skin staining.

Furthermore, because the pigments are formed from the melanin precursors in the hair shaft, the hair colors produced using melanin precursors are permanent. The hair must grow out to return to its original color. Often, consumers prefer to use a temporary hair color that will wash out after one or two shampoos.

The compositions described in PCT patent application Ser. No. US93/11174 filed Nov. 17, 1993 are useful as temporary hair colorants. These compositions contain melanin products which are prepared by forming a complex between a water soluble anionic melanin and selected quaternary compounds, suitably alkyl trimonium halides, alkylalkonium halides or dialkyldimonium halides such as cetrimonium halide or stearalkonium halides. Quaternium-16 and Quaternium-26 are typical commercially available examples of such compounds. These complexes of melanin and the selected quaternary compounds impart a temporary coloring to human hair when deposited thereon in aqueous compositions and thereafter dried. A dye will deposit on the hair to provide a desired color when it is dried by evaporating the water. Although such compositions are acceptable to many consumers, they may not be acceptable to others because they wash off the hair too readily. only rarely do they survive single shampoos. In fact, normally they require a cleave on, treatment since they may be readily removed by even a water rinse.

The art has sought hair coloring compositions which provide colors which are not as difficult to use as the melanin precursors or as permanent, but are more permanent than the colors provided by the above described temporary hair colorants, i.e. dyes which will survive 4 to 6 shampoos or can be mixed with shampoos containing additional dyes in order to freshen temporary hair colors. The hair colorants utilized in the compositions of this invention have these desirable properties.

The compositions of this invention produce in a single treatment step, semi-permanent natural-looking hair color that resist fading in sunlight, resist rub off and resist bleeding in contact with water. The compositions are inexpensive and simple to work with. It has surprisingly been found that aqueous compositions comprising a water soluble quaternized melanin derivative when applied to hair impart a semi-permanent color to the hair which will survive more than three shampoos without loss of color characteristics. A particular advantage of the hair colorants of this invention is that they can be mixed with shampoos containing other hair colorants to freshen the hair color so that the hair color is renewed and retained for an appreciably further period of time. Another is that the products can be used for simultaneous coloring and conditioning of hair. Still another is that the products exhibit the other attributes of natural melanin, i.e. they are antioxidants and free radical scavengers and minimize hair damage caused by oxidants and free radicals often present in the hair after atmospheric exposure.

The products of this invention are also useful for skin care. They may be used alone or, preferably, in conventional skin care compositions. When so employed, they function both as skin colorants to impart a tanned appearance to the treated skin and as sun screen agents to protect the skin from harmful infrared rays.

U.S. Pat. No. 5,006,331 (Gaskin) discloses the use of a melanin composition containing triethanolamine and ferric chloride. The resultant mixture of melanin, triethanolamine and ferric chloride is said to be useful for skin protection, for wound healing and for strengthening hair. An alternate composition contains trypsin in an alkaline medium. Melanin is present in the skin protectant compositions of Gaskin in an amount of from about 0.001 to about 0.09%, along with from about 0.0001% to about 0.27% ferric chloride, both being on a weight basis based on total weight. The skin protectant composition further contains up to about 5% by weight triethanolamine. While not providing a range of concentration for the amount of melanin hydrolysate for the hair protectant compositions according to her invention, Gaskin states at column 6, line 30 that it is present therein in an amount of only about 0.0015% by weight of the total composition. However, this level of Gaskin's melanin hydrolysate is wholly insufficient to impart a color to hair. Moreover, neither of Gaskin's methods provide a melanin material of a cationic character.

PCT Application WO 91/17738 discloses the use of soluble melanin derivatives in a process for producing lightly colored melanins that are aesthetically suitable for use in cosmetic compositions.

WO 94/25532 describes melanin linked to a lipid to form a lipomelanin and its use in a sunscreen product.

It is an object of this invention to provide aqueous compositions for semi-permanently coloring hair using water soluble melanin derivatives.

It is also an object of this invention to provide compositions that will produce a semi-permanent natural-looking hair color that resists fading in sunlight, will not rub off, and will not bleed when in contact with water.

It is further an object of this invention to provide inexpensive compositions for semi-permanently coloring hair using water soluble melanin derivatives.

It is also an object of this invention to provide compositions that are simple to work with for semi-permanently coloring hair using water soluble melanin derivatives.

It is also an object of this invention to provide a one-step process for semi-permanently coloring hair.

It is a further object of this invention to provide compositions for simultaneously coloring and conditioning hair.

It is a still further object of this invention to provide compositions which when used with appropriate shampoos are useful for freshening hair colors.

It is a still further object of this invention to provide products and compositions useful for skin care.

In one aspect of this invention, an aqueous composition is provided for semi-permanently coloring hair comprising a cationic quaternized melanin derivative. Processes for coloring hair are also provided.

SUMMARY OF THE INVENTION

The compounds of this invention are quaternary derivatives of esters or amides obtained by reacting melanin with a hydroxy or amino-substituted quaternary ammonium salt. The hair colorants of this invention are water soluble compounds characterized by an amide or ester linkage between the melanin residue and the quaternary moiety. These compounds may be represented by the formula:

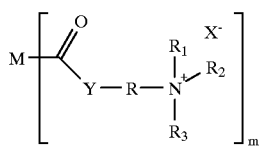

(I)

wherein:

M is a melanin residue,

Y is —O— or NH,

R is a linking group as defined below, $R_1$, $R_2$ and $R_3$ are groups that in combination one with the other and with R quaternize the nitrogen to which they and R are bonded, as defined below, m is the number of derivatized carboxyl groups in the melanin residue, and X is an anion.

The compounds of the present invention may be made by reacting melanin having carboxyl groups with a quaternary ammonium salt, $N^{\oplus}R(YH)R_1R_2R_3 X^-$. $R_1,R_2,R_3$ and R(YH) maybe any chemical group suitable to quaternize the nitrogen to which they are bonded, and that does not prevent ester or amide formation when the melanin and the quaternary salt are reacted. The compounds of the invention may be prepared from any of a wide variety of quaternary compounds that react with carboxyl groups of melanin to produce water soluble quaternized melanin amides or esters. The quaternized melanins of this invention have a cation that intereacts with hair and become attached to the hair by a cation/anion attraction of the cation for the anionic hair. It is this electronic attraction of the cation of the quaternary compound for the anionic charge of the hair which renders the hair colorants of this invention semipermanent rather than temporary as are the hair dyes of the above cited PCT patent application Ser. No. US93/11174 filed Nov. 17, 1993.

Suitably, R may be an unsubstituted or substituted alkylene group having from 1 to 20 carbons, preferably a straight chain unsubstituted alkylene group having 6 to 15 carbons, and $R_1$, $R_2$ or $R_3$ may be an unsubstituted or substituted alkyl group having from 1 to 22 carbons, preferably one of $R_1$, $R_2$ or $R_3$ having from 12 to 16 carbons and two of $R_1$, $R_2$ or $R_3$ having from 1 to 6 carbons. The alkylene and alkyl groups are preferably straight chained. Suitable substituent groups present in R, $R_1$, $R_2$ and $R_3$ may be hydroxy; mono- or polyhydroxyalkyl and alkyloxy, mono- or polyhydroxyalkyloxy, the alkyl group having from 1 to 6 carbons, preferably 1 to 4 carbons, and especially 1 to 2 carbons, with typically up to about 3 hydroxy groups; amino and alkylamino with up to about 6 carbons, preferably 1 to 3 carbons; halo; cyano, and nitro. R, $R_1$, $R_2$ and $R_3$ may also be an unsubstituted or substituted alkylamido group having 1 to 6 carbons, preferably 1 to 3 carbons; an alkylene or dialkylene substituted alicyclic or aryl group, especially phenyl but also cyclohexenyl and naphthyl, the alkylene group(s) having from 1 to 6 carbons, or a heterocyclic such as pyrrole, morpholinyl or piperidinyl. Any of the aryl, alicyclic or heterocyclic groups may be further substituted as set forth above with respect to the alkyl (or alkylene) group. The selection of a substituent group is limited only with regard to whether ester or amide formation would be compromised, and whether the reaction product of the melanin and quaternary is sufficiently soluble to permit formulation in an aqueous-based hair dye product. The substituent groups should not impart instability to the molecule in view of steric hinderance or otherwise.

As previously mentioned the quaternary reactant has at least one amino or hydroxy group YH associated with R that is free to react with an available carboxyl group in the melanin reactant to form an amide or ester compound in accordance with this invention. However, R may have two or more reactive hydroxy or amino groups associated with it. Similarly, any of $R_1$, $R_2$ and $R_3$ may also have one or more additional hydroxy or amino groups. When multiple reaction sites are available for amide or ester formation, the reaction will take place at one of them. The other substituents present on R, $R_1$, $R_2$ and $R_3$ of the quaternary reactant are chemically compatible with respect to ester or amide formation but may be further reacted to produce desired colors.

The above identified products are especially preferred when they are prepared from quaternary compounds containing an unsubstituted aminoalkylene or hydroxyalkylene group together with at least one other long chain alkyl group attached to the positively charged nitrogen. The most preferred products of the invention are those which contain at least one long chain alkyl group and at least one short chain alkyl group containing from about 1 to 6 carbon atoms, suitably methyl or ethyl. Although the invention contemplates products in which all of the R groups are long chain, these are not preferred because they are difficult to prepare due, principally, to steric hindrance.

Suitable quaternary materials that may be used in the practice of this invention are set forth, generally, in the CTFA Cosmetic Ingredient Handbook (1st Ed., 1988) at pages 40–42 (quaternary ammonium compounds). The entire disclosure of this citation is incorporated herein by reference. Suitability of specific compounds may be determined by one of ordinary skill in the hair dye art by simple experimentation. They are positively charged tetra-substituted nitrogen derivatives having at least one counterion which is an anionic moiety, e.g., a halide or methosulfate. Using the nomenclature of the CrFA Handbook, which is widely used and accepted by chemists in the cosmetic art, illustrative cationic materials are hydroxy or amino alkyl trimonium halides, alkylalkonium halides and the dialkyldimonium halides, wherein the alkyl groups have about 1 to about 22 carbons and the halide is Cl or Br. Useful quaternium compounds include for example, the quaternium series of compound such as Quaternium 16, 22, 30, 36, 46, 78, 79, 80 and 82. Other suitable quaternary reactants will be readily apparent to the skilled artisan after the benefit of this disclosure.

It will be apparent from the foregoing that the quaternary compounds may contain a variety of functional groups both in the main chain or attached thereto.

The melanin residue or moiety is that portion of the melanin which remains after the formation of the ester or amide bond by reaction with the quaternary compound. It will be appreciated that melanin whether soluble or insoluble is a mixture of several similar molecules characterized in one respect by the presence of carboxyl groups. In the formation of the products of this invention, only a few of those groups or a very large proportion of them may react. The important criterion is that the reaction product be soluble and cationic. The reaction can be controlled by the usual procedures employed by the skilled artisan, principally by selection of the relative amounts of each reactant. In that connection, it should be noted that two or even more different quaternary compounds can be employed in a specific reaction to achieve mixtures of quaternized melanins.

In most instances, it is doubtful that all of the carboxyl groups will react. Some of them may not be available for reaction because of steric hindrance caused either by the structure of the melanin, the size of the substituents on the quaternary compound or a combination of these factors. Therefore, in the general formula set forth above and in the claims, m is defined as the number of carboxyl groups in the melanin residue which have reacted and therefore have become derivatized by forming water soluble esters or amides.

An important feature of the reaction which produces the products of this invention is that more than half of the available carboxyl groups are permitted to react in the formation of esters or amides. If less than half of these acidic groups react, the resulting product is anionic rather than cationic. Since, as noted above, hair is anionic it will repel rather than attract the hair colorants. The hair colorants of this invention must be cationic.

Another characteristic of the reactants employed to form the products of the invention is that both water soluble and insoluble melanins may be employed as starting materials. Water soluble reactants are preferred since they contain a larger number of carboxyl groups. They may be prepared from insoluble melanins by a number of known procedures, for example utilizing hydrogen peroxide as described by Wolfram, et al, *The Mechanism of Hair Bleaching,* J. Soc. Cosmet. Chem., 21:875–900 (1970).

The anion in the products of this invention may be any of those normally associated with quaternary compounds so long as the products produced are water soluble. Typically they are halides, preferably chlorides or bromides.

DETAILED DESCRIPTION OF THE INVENTION

The products of the invention may be formed by any of the usual methods of forming amides or esters.

For example, to form amides, melanin free acid may be reacted with an aminoalkyl substituted quaternary compound in an aqueous buffer at a pH of about 7 at ambient temperature in the presence of a carbodiimide such as 1-ethyl-1,2-(3-dimethylaminopropyl) carbodiimide.

Esters may be prepared for example, by reacting equimolar quantities of the reactants in an aqueous buffer at pH 7.

Both procedures are illustrated in the examples.

The melanin that is useful in this invention may be synthetic or obtained from natural sources such as human, primate, bovine and other animals. In particular, squid melanin (sepia melanin) is commercially available. The source of the melanin is not critical. As used herein, the term "melanin" refers to the insoluble pigment and should be understood to include both natural and synthetic melanin.

Synthetic melanin may be obtained by a number of procedures known to those skilled in the art. The principal procedures are oxidative polymerization methods in which melanin intermediates such as 5,6-dihydroxyindole-2-carboxylic acid (DHICA), dihydroxy indole (DHI), dihydroxy-phenylalanine (DOPA) and the like are treated with an oxidizing agent such as, for example, hydrogen peroxide/iodide, potassium ferricyanide, potassium permanganate or ammonium persulfate. These procedures are well known and are described, for example in U.S. Pat. Nos. 5,173,085; 5,346,509; 5,273,550 and 4,804,385, the entire disclosures of which are incorporated herein by reference.

The amount of quaternized melanin product required in the composition of this invention will vary according to factors such as the carrier used, the initial hair color of the user prior to dyeing, the desired end hair color and other factors well known to the skilled artisan. A tinctorially effective amount of hair colorant should be used. In general, the amount required is at least about 0.1%, typically from about 0.1% up to its solubility limit in the composition, but generally less than about 5.0%, and preferably from about 0.2% to about 3.0%, all concentrations being on a weight basis based on the total weight of the composition.

Skin compositions employing the products of this invention are generally less concentrated than those used as hair colorants. Typically, they will contain from about 0.01% to 10%, preferably 0.05% to 1% of at least one product of the invention dissolved, emulsified or suspended in a pharmaceutically acceptable skin vehicle which may be aqueous or non-aqueous and may comprise water, inert oils, emollients, surfactants, buffers or other additives such as those illustrated in the examples.

Although the pH of the aqueous hair coloring compositions of this invention may not be so low or high as to damage hair or skin, the compositions are useful at a wide range of pH values. The correct pH for a particular composition will vary with the product employed. In general, however, the pH of the composition will be about 3 to about 10, preferably 5 to 10.

In addition to the selected hair colorant or mixture of hair colorants, it may be desirable to include cosmetically acceptable carriers in the hair colorant compositions of this invention. Acceptable carriers vary from simple solutions or dispersions with aqueous or alcoholic solvents, to complex mixtures that contain thickeners or other agents. The carriers that may be used in accordance with this invention must be compatible with the selected dye.

It may also be desirable to include in the compositions of this invention adjuvants or additives that are commonly found in such compositions, in amounts effective to provide their intended function. Such adjuvants or additives include, for example, solvents, solubilizing agents, surfactants, thickening agents, alkalizing agents, chelating agents, preservatives and fragrances.

The solvents that may be used include organic solvents or solvent systems that are compatible with the other components. A number of organic solvents are known in the art that are useful for such purposes. These organic solvents include alcohols, particularly alkyl alcohols of 1–6 carbons, especially ethanol and propanol; and glycols of up to about 10 carbons, especially diethyleneglycol; monobutyl ether; carbitols and benzyl alcohol.

The thickening agents that may be used in this invention include polyvinylpyrrolidone, gum arabic, cellulose derivatives such as methylcellulose or hydroxyethylcellulose, and inorganic thickeners such as bentonite. The additional solubilizing agents that may be employed include for example, ethoxylated fatty alcohols. The preservatives that may be used include: methyl- and propyl parababen, 2-phenoxyethanol, DMDMH, and Kathon CG.

A special advantage of the products of this invention is that certain of them can be employed to both color and condition the hair at the same time. It is known that when long chain alkyl substituents containing certain quaternary ammonium salts are deposited on human hair, they improve combability i.e. the relative ease with which hair can be combed, by imparting a certain lubricity to the hair as well as by providing an antistatic effect. Both of these effects combine to make the hair easier to manage so that the desired appearance of the hair can be more readily achieved. Compositions having these properties are called "hair conditioners". See, for example, A. C. Lunn and R. E. Evans, The Electrostatic Properties of Human Hair, J. Soc. Cosmet, Chem., 28, 549 (1977).

Products of this invention formed from quaternary reactants having up to two substituted or unsubstituted alkyl groups containing from about 12 to about 16 carbon atoms are preferred for both colorant and conditioning properties. Quaternary reactants which are useful for such concurrent activity include for example, several of those Quaternium compounds mentioned above.

In another preferred aspect of the invention, the water soluble products of the invention are incorporated into a shampoo base which may also contain auxiliary hair colorants to effect simultaneous coloring and cleaning of the hair. This feature of the invention is especially useful to freshen the color of previously dyed hair.

Shampoos are well known to those skilled in the art and need not be described with any particularity. In general, they are aqueous solutions containing from about 1% to about 50% by weight of a surfactant which may be cationic, anionic, non-ionic or amphoteric. Suitable surfactants include for example, behenealkonium chloride, dodecyldimonium chloride, sodium lauryl sulfate, sodium laureth sulfate, cocamidopropyl betaine and cocamidopropyl sultaine. Other useful surfactants may be identified by resort to McCutcheon's Emulsifiers and Detergents (North Amer. Edition 1987) which is incorporated herein by reference. With the compositions of this invention, the amount of surfactant is about the same as employed in conventional shampoos.

It will be appreciated that none of the various additives described above can be employed in the compositions if they insolubilize the hair colorants of the invention at any concentration.

A further aspect of the present invention is the optional incorporation of one or more known hair color modifiers in the compositions of the invention. These include for example, direct dyes, primary intermediates and couplers.

The concentration of hair color modifier is normally less than about 10 mg/ml, and preferably is present in the reaction medium at from about 0.01 to about 5 mg/ml, most preferably from about 0.05 to about 2 mg/ml. The amount of these components should not be so great as to cause precipitation of the hair colorants of the invention.

A wide variety of direct dyes, primary intermediates and couplers are known to the skilled artisan and can be employed in this invention.

The presently preferred primary intermediates and couplers with which they will react include:

Primary Intermediates:
p-phenylenediamine
p-aminophenol
o-aminophenol
N, N-bis(2-hydroxyethyl)-p-phenylenediamine
2,5-diaminopyridine
p-toluenediamine
Couplers:
resorcinol
m-aminophenol
α-naphthol
5-amino-o-cresol
2-methylresorcinol
4,6-di(hydroxyethoxy)-m-phenylenediamine
m-phenylenediamine Suitable direct dyes include, for example nitro dyes, azo dyes and anthraquinone dyes.

This invention provides processes for coloring hair or treating skin which comprises applying to the hair or skin an aqueous composition of the invention. The compositions may be applied to the hair by conventional techniques known in the art. For example, they can be poured over the hair or applied with an applicator. The amount of time for which the dye composition must be in contact with the hair is not critical. It may vary from about 2 minutes to about 50 minutes, but is usually from about 5 minutes to about 30 minutes. A composition for skin care may be applied to the skin as a liquid or as a viscous composition such as a cream or ointment.

The invention also includes kits containing a composition of this invention. A kit may comprise one container which contains a composition including all of the various components described above. Alternatively, there may be two or more containers each containing separate components which are mixed during or just prior to application to the hair or skin.

The hair coloring effects achieved with the products of this invention may be evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greeness., Similarly, positive b values indicate yellowness, while negative b values indicate blueness. The L parameter is a measure of color intensity, and has a value of 0 for absolute black to 100 for absolute white.

The following non-limiting examples are given by way of illustration only. In the examples, the formation of a cationic, positively charged pigment was shown by electrophoretic measurements in 0.05M sodium borate buffer, pH 9 at 250 Volts.

EXAMPLES

Abbreviations used: MFA (Melanin free acid) is; sepia melanin, made water soluble by treatment with $H_2O_2$. MES buffer is morpholinoethylsulphonate. EDC is 1-ethyl-3-(3-dimethylaminopropyl)carbodiimide. DHICA is 5,6-dihydroxyindole-2-carboxylic acid.

Example 1

MFA/2-AMINOETHYL TRIMETHYLAMMONIUM CHLORIDE

To a solution of MFA (500 mg) in 0.1M MES buffer pH 7.0 (100 ml), 1.6 g of 2-aminoethyl trimethylammonium chloride hydrochloride is added, care being taken to maintain the pH at 7.0. The solution is stirred for 10 minutes and then EDC (750 mg) is added. After 5 h, another 750 mg portion of EDC is added with continuing stirring and the mixture is left overnight at room temperature. The pigment thus obtained is dialyzed against water over a period of 48 h and then is collected by evaporation of the solvent.

Example 2

MFA/QUATERNIUM 22

To a solution of MFA (500 mg) in 0.1M MES buffer, pH 7.0 (120 ml), 3.33 ml of Quaternium 22 are added with stirring. One gram of EDC is added followed by another 1 g portion after 4 h and the mixture is left under vigorous stirring at room temperature overnight. The pigment thus formed is dialyzed against water over 24 h and then is evaporated to dryness.

Example 3

MFA/QUATERNIUM 22

A 1% solution of the product of Example 2 in pH 10 buffer was prepared and applied to (bleached) hair for 15 minutes. Afterwards, the hair was rinsed with water and dried.

| Hunter | L | a | b |
| --- | --- | --- | --- |
| before treatment | 64.0 | 1.4 | 18.9 |
| after treatment | 50.2 | 2.2 | 14.5 |

If the hair was treated as described above, but using unmodified MFA instead of MFA/Quaternium 22 pigment, there was no noticeable color change imparted to the hair (Hunter values L 61.3 a 1.5 b 17.3).

Example 4

MFA/AMINOETHYL TRIMETHYLAMMONIUM CHLORIDE

A 1% solution of the product of Example 1 in pH 10 buffer was prepared and applied to (bleached) hair for 15 minutes. Afterwards, the hair was rinsed with water and dried.

| Hunter | L | a | b |
| --- | --- | --- | --- |
| before treatment | 64.0 | 1.4 | 18.9 |
| after treatment | 56.5 | 2.0 | 16.3 |

If the hair was treated as described above, but using unmodified MFA instead of MFA/aminoethyl trimethylammonium pigment, there was no noticeable color change imparted to the hair (Hunter values L 61.3 a 1.5 b 17.3).

Example 5

A sunscreen composition is prepared by thoroughly mixing the following components:

| DHICA/Quaternium 22 | 0.1 |
| --- | --- |
| Ethyl dihydroxypropyl PABA | 2.0 |
| Propylene Glycol | 20.0 |
| Oleth-20 | 4.7 |
| Laneth-16 | 4.7 |
| water | 68.5 |

When applied to the skin the composition afforded protection against sun rays.

Example 6

A skin care composition is prepared by thoroughly mixing the following components:

| DHICA/Quaternium 22 | 0.1% |
| --- | --- |
| Methyl Cellulose | 0.5% |
| Glycerin | 2.0% |
| Ethanol | 10.0% |
| Water | 85.5% |
| Fragrance | Q.S. 100% |

When applied to the skin, the composition imparted a darker color.

What is claimed is:

1. A water soluble cationic compound that is an amide or ester obtained by reacting a melanin with a quaternary salt having at least one reactive amino or hydroxyl group.

2. The water soluble cationic compound of claim 1 having the formula:

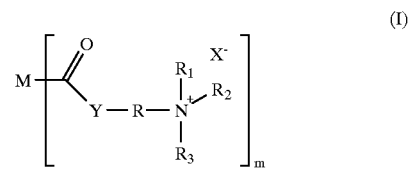

wherein:

M is a melanin residue,

Y is —O— or NH,

R, $R_1$, $R_2$ and $R_3$ are groups that in combination one with the other quaternize the nitrogen to which they are bonded, m is the number of derivatized carboxyl groups in the melanin residue, and X is an anion.

3. The compound of claim 2 in which:

R is alkylene group of from 1 to 20 carbons; an amidoalkyl group, the alkyl having from 1 to 6 carbons; an alkylene- or dialkylene-substituted aryl or alicyclic group, the alkylene group(s) having from 1 to 6 carbons, and a heterocyclic group selected from the group consisting of morpholinyl, piperidinyl and pyrrole, and $R_1$, $R_2$ and $R_3$, which may be the same or different, are alkyls of from 1 to 22 carbons, an alkylamido group, the alkyl having from 1 to 6 carbons; an alkyl- or dialkyl-substituted aryl or alicyclic group, the alkyl group(s) having from 1 to 6 carbons and a heterocyclic group selected from the group consisting of morpholinyl, piperidinyl and pyrrole, each group R, $R_1$, $R_2$ and $R_3$ being unsubstituted or substituted with a substituent that does not prevent ester or amide formation, the substituents being selected from the groups consisting of hydroxy; mono- or polyhydroxyalkyl having from 1 to 6 carbons and from 1 to 3 hydroxy groups; alkloxy, mono- or polyhydroxyalkyloxy having from 1 to 6 carbons and from 0 to 3 hydroxy groups; amino and alkylamino having from 1 to 6 carbons in the alkyl group; amidoalkyl having from 1 to 6 carbons; halo; cyano, and nitro.

4. The compound of claim 3 wherein R is an alkylene and has from 6 to 15 carbons, and at least two of $R_1$, $R_2$ or $R_3$ are alkyl having from 1 to 6 carbons, not more than two of $R_1$, $R_2$ and $R_3$ being substituted with a group selected from the group consisting of hydroxy; mono- or polyhydroxyalkyl having from 1 to 4 carbons and from 1 to 3 hydroxy groups; alkloxy, mono- or polyhydroxyalkyloxy having from 1 to 4 carbons and from 0 to 3 hydroxy groups; amino and alkylamino having from 1 to 3 carbons in the alkyl group; amidoalkyl having from 1 to 3 carbons; halo; cyano, and nitro.

5. A composition comprising in an amount effective to color hair or treat skin, a compound having the formula:

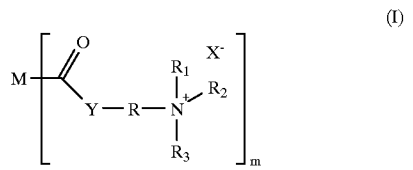

wherein:
M is a melanin residue,
Y is —O— or NH,
R, $R_1$, $R_2$ and $R_3$ are groups that in combination one with the other quaternize the nitrogen to which they and R are bonded,
m is the number of derivatized carboxyl groups in the melanin residue, and
X is an anion, and
a cosmetically acceptable vehicle.

6. The composition of claim 5 in which:
R is alkylene group of from 1 to 20 carbons; an amidoalkyl group, the alkyl having from 1 to 6 carbons; an alkylene- or dialkylene-substituted aryl or alicyclic group, the alkylene group(s) having from 1 to 6 carbons, and a heterocyclic group selected from the group consisting of morpholinyl, piperidinyl and pyrrole, and
$R_1$, $R_2$ and $R_3$, which may be the same or different, are alkyls of from 1 to 22 carbons, an alkylamido group, the alkyl having from 1 to 6 carbons; an alkyl- or dialkyl-substituted aryl or alicyclic group, the alkyl group(s) having from 1 to 6 carbons and a heterocyclic group selected from the group consisting of morpholinyl, piperidinyl and pyrrole, each group R, $R_1$, $R_2$ and $R_3$ being unsubstituted or substituted with a substituent that does not prevent ester or amide formation, the substituents being selected from the group consisting of hydroxy; mono- or polyhydroxyalkyl having from 1 to 6 carbons and from 1 to 3 hydroxy groups; alkloxy, mono- or polyhydroxyalkyloxy having from 1 to 6 carbons and from 0 to 3 hydroxy groups; amino and alkylamino having from 1 to 6 carbons in the alkyl group; amidoalkyl having from 1 to 6 carbons; halo; cyano, and nitro.

7. The composition of claim 5 wherein R is an alkylene and has from 6 to 15 carbons, and $R_1$, $R_2$ at least two of $R_1$, $R_2$ or $R_3$ are alkyl having from 1 to 6 carbons, not more than two of $R_1$, $R_2$ and $R_3$ being substituted with a group selected from the group consisting of hydroxy; mono- or polyhydroxyalkl having from 1 to 4 carbons and from 1 to 3 hydroxy groups; alkloxy, mono- or polyhydroxyalkyloxy having from 1 to 4 carbons and from 0 to 3 hydroxy groups; amino and alkylamino having from 1 to 3 carbons in the alkyl group; amidoalkyl having from 1 to 3 carbons; halo; cyano, and nitro.

8. A method of coloring hair (or skin) which comprises contacting hair (or skin) with an effective hair dyeing (or skin treating) amount of a compound of the formula:

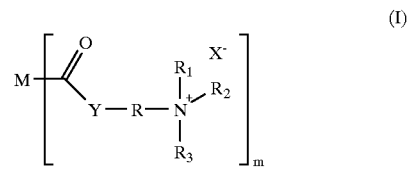

wherein:
M is a melanin residue,
Y is —O— or NH,
R, $R_1$, $R_2$ and $R_3$ are groups that in combination one with the other quaternize the nitrogen to which they and R are bonded,
m is the number of derivatized carboxyl groups in the melanin residue, and
X is an anion.

9. The method of claim 8 in which:
R is alkylene group of from 1 to 20 carbons; an amido alkyl group, the alkyl having from 1 to 6 carbons; an alkylene- or dialkylene-substituted aryl or alicyclic group, the alkylene group (s) having from 1 to 6 carbons, and a heterocyclic group selected from the group consisting of morpholinyl, piperidinyl and pyrrole, and
$R_1$, $R_2$ and $R_3$, which may be the same or different, are alkyls of from 1 to 22 carbons, an alkylamido group, the alkyl having from 1 to 6 carbons; an alkyl- or dialkyl--substituted aryl or alicyclic group, the alkyl group(s) having from 1 to 6 carbons and a heterocyclic group selected from the group consisting of morpholinyl, piperidinyl and pyrolle, each group R, $R_1$, $R_2$ and $R_3$ being unsubstituted or substituted with a substituent: that does not prevent ester or amide formation, the substituents being selected from the groups consisting of hydroxy; mono- or polyhydroxyalkl having from 1 to 4 carbons and from 1 to 3 hydroxy groups; alkloxy, mono- or polyhydroxyalkyloxy having from 1 to 4 carbons and from 0 to 3 hydroxy groups; amino and alkylamino having from 1 to 6 carbons in the alkyl group; amidoalkyl having from 1 to 6 carbons; halo; cyano, and nitro.

10. The method of claim 9 wherein R is an alkylene and has from 6 to 15 carbons, and $R_1$, $R_2$ at least two of $R_1$, $R_2$ or $R_3$ are alkyl having from 1 to 6 carbons, not more than two of $R_1$, $R_2$ and $R_3$ being substituted with a group selected from the group consisting of hydroxy; mono- or polyhydroxyalkl having from 1 to 2 carbons and from 1 to 3 hydroxy groups; alkloxy, mono- or polyhydroxyalkyloxy having from 1 to 2 carbons and from 0 to 3 hydroxy groups; amino and alkylamino having from 1 to 3 carbons in the alkyl group; amidoalkyl having from 1 to 3 carbons; halo; cyano, and nitro.

11. The compound of claim 1 wherein the melanin is water soluble and the quaternary salt is selected from the group consisting of alkyltrimonium halides, alkylalkonium halides and dialkyldimonium halides, the alkyl group having 1 to 22 carbons.

12. The compound of claim 11 wherein the quaternary salt is 2-aminoethyltrimethyl ammonium chloride.

13. The compound of claim 11 wherein the melanin is melanin free acid.

14. The compound of claim 12 wherein the melanin is melanin free acid.

15. The compound of claim 1 wherein the melanin is water soluble and wherein the quaternary salt is selected from the group consisting of Quaternium 16 Quaternium 22, Quaternium 30, Quaternium 36, Quaternium 46, Quaternium 78, Quaternium 79, Quaternium 80, and Quaternium 82.

16. The compound of claim 15 wherein the quaternary salt is Quaternium 22.

17. The compound of claim 15 wherein the quaternary salt is Quaternium 16.

18. The compound of claim 15 wherein the quaternary salt is Quaternium 30.

19. The compound of claim 15 wherein the quaternary salt is Quaternium 80.

20. The compound of claim 15 wherein the quaternary salt is Quaternium 82.

21. The compound of claim 15 wherein the melanin is melanin free acid.

22. The compound of claim 16 wherein the melanin is melanin free acid.

23. A composition comprising a water soluble cationic compound that is an amide or ester obtained by reacting a melanin with a quaternary salt having at least one reactive amino or hydroxyl group, said cationic compound being present in the composition in an amount effective to dye hair or treat skin, and a cosmetically acceptable vehicle.

24. The composition of claim 23 wherein the melanin is water soluble and the quaternary salt is selected from the group consisting of alkyltrimonium halides, alkylalkonium halides and dialkyldimonium halides, the alkyl group having 1 to 22 carbons, Quaternium 16, Quaternium 22, Quaternium 30, Quaternium 36, Quaternium 46, Quaternium 78, Quaternium 79, Quaternium 80., and Quaternium 82.

25. The composition of claim 24 wherein the melanin is melanin free acid and the quaternary salt is 2-aminoethyltrimethyl ammonium chloride.

26. The composition of claim 24 wherein the melanin is melanin free acid and the quaternary salt is Quaternium 22.

27. A method of coloring hair (or skin) which comprises contacting the hair (or skin) with an effective hair dyeing (or skin treating) amount of the compound of claim 11.

28. The method of claim 27 wherein the melanin is melanin free acid and the quaternary salt is 2-aminoethyltrimethyl ammonium chloride.

29. A method of coloring hair (or skin) which comprises contacting the hair (or skin) with an effective hair dyeing (or skin treating) amount of the compound of claim 15.

30. The method of claim 29 wherein the melanin is melanin free acid and the quaternary salt is Quaternium 22.

* * * * *